United States Patent
Sailor et al.

(10) Patent No.: US 8,097,173 B2
(45) Date of Patent: Jan. 17, 2012

(54) MAGNETIC POROUS PARTICLES AND METHOD OF MAKING

(75) Inventors: Michael J. Sailor, La Jolla, CA (US); Yang Yang Li, Irvine, CA (US); Nathan Trujillo, San Diego, CA (US); Jason Dorvee, Ithaca, NY (US)

(73) Assignee: The Regents of the University of California, Oakland, CA (US)

( * ) Notice: Subject to any disclaimer, the term of this patent is extended or adjusted under 35 U.S.C. 154(b) by 1258 days.

(21) Appl. No.: 11/632,914

(22) PCT Filed: Jul. 18, 2005

(86) PCT No.: PCT/US2005/025383
§ 371 (c)(1),
(2), (4) Date: Jan. 18, 2007

(87) PCT Pub. No.: WO2007/008211
PCT Pub. Date: Jan. 18, 2007

(65) Prior Publication Data
US 2008/0296255 A1   Dec. 4, 2008

Related U.S. Application Data

(60) Provisional application No. 60/589,171, filed on Jul. 19, 2004.

(51) Int. Cl.
*C23F 1/00* (2006.01)
*B44C 1/22* (2006.01)
*B29D 11/00* (2006.01)
*B32B 5/16* (2006.01)
*B32B 15/00* (2006.01)

(52) U.S. Cl. .......... 216/2; 216/22; 216/24; 216/56; 428/357; 428/402; 428/403; 428/692.1; 977/838; 977/960; 977/962

(58) Field of Classification Search ............ 216/2, 22, 216/24, 56; 428/212, 217, 218, 402, 403, 428/357, 692.1; 977/838, 960, 962
See application file for complete search history.

(56) References Cited

U.S. PATENT DOCUMENTS
6,130,748 A * 10/2000 Kruger et al. .......... 356/450
(Continued)

FOREIGN PATENT DOCUMENTS
WO    WO 2005/034725    *   4/2005
(Continued)

OTHER PUBLICATIONS

Hamadache, F. et al, Electrodeposition of Fe-Co alloys into nanoporous p-type silicon: Influence of the electrolyte composition, J. Mater. Res., Vol. 17, No. 5, May 2002, pp. 1074-1084, especially p. 1075 and Fig. 1.*

(Continued)

*Primary Examiner* — Nadine G Norton
*Assistant Examiner* — Christopher Remavege
(74) *Attorney, Agent, or Firm* — Greer, Burns & Crain Ltd.

(57) ABSTRACT

The invention provides porous particles that produce a predetermined optical response and that may be manipulated magnetically. A preferred particle of the invention has a porous structure that produces a predetermined optical response and magnetic material adhered to the particle. Another preferred particle is amphiphilic. The optical response provided by a particle of the invention enables particles of the invention to be used in sensing, labeling, signaling, display and many other applications. The magnetic nature of the present magnetic particles permits the particles themselves to be manipulated, e.g., vibrated, moved and re-oriented. The porous particles can also be used to control, move, and/or deliver small volumes of liquids and solids associated with the particles.

22 Claims, 7 Drawing Sheets

U.S. PATENT DOCUMENTS

| | | | |
|---|---|---|---|
| 6,248,539 B1 * | 6/2001 | Ghadiri et al. | |
| 6,660,381 B2 * | 12/2003 | Halas et al. | 428/403 |
| 6,786,968 B2 * | 9/2004 | Theil | 117/93 |
| 7,042,570 B2 * | 5/2006 | Sailor et al. | |
| 7,078,095 B2 * | 7/2006 | Tam | 428/352 |
| 7,167,605 B2 * | 1/2007 | Chang et al. | |
| 7,433,811 B2 * | 10/2008 | Gao et al. | |
| 7,575,645 B2 * | 8/2009 | Igarashi et al. | 148/312 |
| 2004/0086885 A1 * | 5/2004 | Lee et al. | 435/6 |
| 2005/0042764 A1 * | 2/2005 | Sailor et al. | |
| 2006/0141466 A1 * | 6/2006 | Pinet et al. | 435/6 |
| 2007/0051815 A1 * | 3/2007 | Sailor et al. | |
| 2007/0148695 A1 * | 6/2007 | Sailor et al. | |
| 2008/0220231 A1 * | 9/2008 | Suetsuna et al. | 428/216 |
| 2008/0297878 A1 * | 12/2008 | Brown et al. | 359/263 |
| 2009/0179171 A1 * | 7/2009 | Sailor et al. | 252/62.51 R |

FOREIGN PATENT DOCUMENTS

| WO | WO 2005/062865 | * | 7/2005 |
|---|---|---|---|

OTHER PUBLICATIONS

Schmedake, T.A., et al, Standoff Detection of Chemicals Using Porous Silicon "Smart Dust" Particles, Adv. Mater., vol. 14, No. 18, Sep. 16, 2002, pp. 1270-1272, especially Experimental section.*

Gusev, S.A., et al, Ferromagnetic filaments fabrication in porous Si matrix (invited), J. Appl. Phys., vol. 76. No. 10. Nov. 15, 1994, pp. 6671-6672.*

Rudge, S.R., Preparation, characterization, and performance of magnetic iron-carbon composite microparticles for chemotherapy, Biomaterials, vol. 21, 2000, pp. 1411-1420, especially pp. 1413 and 1414.*

Anker, Jeffrey N., "Magnetically modulated optical nanoprobes", Feb. 17, 2003, "Applied Physics Letter", vol. 82, No. 7, pp. 1102-1104.*

Spherotech, Inc., "SPHERO Ferromagnetic Particles", source: http://www.spherotech.com/Magnetic%20Beads%20catalog%202010-2011%20rev%20a.pdf.*

H. Arwin et al. "Protein adsorption in thin porous silicon layers", Phys. Stat. Sol. A, Vo.. 182, pp. 515-520 (2000).

P. Aussillous et al., "Liquid Marbles", Nature, vol. 411, pp. 924-927 (Jun. 21, 2001).

S.C. Bayliss et al., "The culture of mammalian cells on nanostructured silicon", Advanced Materials, vol. 11, pp. 318-321 (1999).

P. Berger et al., "Preparation and properties of an aqueous ferrofluid", J. Chem. Educ., vol. 76, pp. 943-948 (Jul. 1999).

M.G. Berger et al., Dielectric filters made of PS: advanced performance by oxidation and new layer structures. Thin Sol. Films, vol. 297, pp. 237-240 (1997).

R. Boukherroub, "Thermal hydrosilylation of undecylenic acid with porous silicon.", J. Electrochem. Soc., vol. 149, No. 2, pp. 59-63 (2002).

S. Chan et al., "Identification of gram negative bacteria using nanoscale silicon microcavities", J. Am. Chem. Soc., vol. 123, 11797-98 (2001).

V. Chin et al., "Compatibility Of Primary Hepatocytes With Oxidized Nanoporous Silicon",. Advanced Materials, vol. 13, pp. 1877-1880 (Dec. 17, 2001).

B.E. Collins et al., "Determining Protein Size Using an Electrochemically Machined Pore Gradient in Silicon:", Advanced Functional Materials, vol. 12, pp. 187-191 (Mar. 3, 2002).

F. Cunin et al., "Biomolecular screening with encoded porous silicon photonic crystals", Nature Materials, vol. 1, pp. 39-41 (Sep. 2002).

J. Hong et al., "Integrated nanoliter systems", Nature Biotechnology, vol. 21, No. 10,. 1179-1183 (Oct. 2003).

J.R. Link, "Smart Dust: Self-assembling, self-orienting photonic crystals of porous Si.", Applied Physical Science, vol. 100, No. 19, pp. 10607-10610 (Sep. 16, 2003).

J. Liu et al., "Solving the 'world-to-chip' interface problem with a microfluidic matrix", Anal. Chem. vol. 75, 4718-23 (Sep. 15, 2003).

T.A. Schmedake et al., "Standoff Detection of Chemicals using Porous Silicon 'Smart Dust' Particles", Advanced Materials, vol. 14, pp. 1270-1272 (Sep. 16, 2002).

P.A. Snow et al., "Vapor sensing using the optical properties of porous silicon Bragg mirrors", Journal of Applied Physics, vol. 86, No. 4, pp. 1781-1784 (Aug. 15, 1999).

V. Srinivasan et al., "Droplet-based microfluidic lab-on-a-chip for glucose detection", Analytica Chimica Acta, vol. 507, 145-150 (2004).

M.P. Stewart et al, "Photopatterned Hydrosilylation on Porous Silicon", Angew. Chem. Int. Ed., vol. 37, No. 23, pp. 3257-3260 (1998).

A. Urbas et al., "One-Dimensionally Periodic Dielectric Reflectors from Self-Assembled Block Copolymer-Homopolymer Blends", Macromolecules, vol. 32, 4748-50, 1999.

O.D. Velev et al., "On-chip manipulation of free droplets", Nature, vol. 426, 515-516 (Dec. 4, 2003).

G. Vincent, "Optical properties of porous silicon superlattices", Appl. Phys. Lett., vol. 64, pp. 2367-2369 (May 2, 1994).

B. Zheng et al., "A droplet-based, composite PDMS/glass capillary microfluidic system for evaluating protein crystallization conditions by microbatch and vapor-diffusion methods with on-chip X-ray diffraction", Angew. Chem. Int. Ed., vol. 43, pp. 2508-2511 (2004).

M.J. Sailor, "Sensor Applications of Porous Silicon", (ed. Canham, L.) (Short Run Press, London), Aug. 1997, pp. 364-370.

L.T. Canham, "Biomedical Applications of Porous Silicon", (ed. Canham, L.) (Short Run Press, London), Aug. 1997, pp. 371-376.

W. Lang, "Micromachining Applications of Porous Silicon", (ed. Canham, L.) (Short Run Press, London), Aug. 1997, pp. 377-383.

S.O. Meade, M.S. Yoon, K.H. Ahn, M.J. Sailor, "Porous Silicon Photonic Crystals as Encoded Microcarriers", Adv. Materials, vol. 16, No. 20, Oct. 18, 2004, pp. 1811-1814.

Millman, Jeffrey R., et. al., "Anistropic panicle synthesis in dielectrophoretically controlled microdroplet reactors", Nature Materials. vol. 4, Jan. 2005.*

* cited by examiner

MAGNETIC POROUS PARTICLES AND METHOD OF MAKING

PRIORITY CLAIM

Applicants claim priority benefits under 35 U.S.C. §119 on the basis of Patent Application No. 60/589,171, filed Jul. 19, 2004.

STATEMENT OF GOVERNMENT INTEREST

The invention was made with Government support under NIH Grant Number N01-CO-37117 awarded by the National Institutes of Health, and under Air Force Office of Scientific Research Grant Number F49620-02-1-0288. The Government has certain rights in this invention.

FIELD OF THE INVENTION

A field of the invention is optoelectronics. Another exemplary field of the invention is optical structure fabrication. Another exemplary field of the invention is encoding. Additional exemplary fields of the invention include the life sciences, security, product marking, food processing, agriculture, and chemical detection. Still another field of the invention is microfluidics. Yet another exemplary field of the invention is transport of liquids and solids using magnetic fields.

BACKGROUND

Porous particles constructed from electrochemically etched porous materials, such as silicon, have widespread application in optoelectronics, chemical and biological sensors, high-throughput screening, and drug delivery applications. These porous particles are especially advantageous because of the relative ease with which the optical properties, pore size, and surface chemistry can be manipulated. Moreover, position, width, and intensity of spectral reflectivity peaks may be controlled by the current density waveform and solution composition used in the electrochemical etch, thus rendering possible the preparation of films of porous particles that display any color within the visible light band with high color saturation, which is a desirable feature for information displays.

A well-appreciated need for labeling exists in society. Labeling is a fundamental basis for tracking and identifying. Encoding can be used as a form of labeling understood by persons or equipment, as in the case of bar coding. At the microscale, however, labeling/encoding itself becomes difficult.

Porous particles and films constructed from electrochemically etched porous materials have provided powerful methods for labeling and encoding. Porous particles and films and methods using such are disclosed in 1) U.S. Published Patent Application 20050042764, entitled "Optically encoded particles" to Sailor et al., published Feb. 24, 2005; 2) U.S. Published Patent Application 20050009374, entitled "Direct patterning of silicon by photoelectrochemical etching", to Gao, et al., published Jan. 13, 2005, now U.S. Pat. No. 7,433,811, issued Oct. 7, 2008; 3) U.S. Published Patent Application 20030146109 entitled "Porous thin film time-varying reflectivity analysis of samples," to Sailor, et al. published Aug. 7, 2003, now U.S. Pat. No. 7,042,570, issued May 9, 2006; 4) PCT Application PCT/US04/043001, entitled "Optically encoded particles, system and high throughput screening, to Sailor et al, filed Dec. 21, 2004, now U.S. Publication No. US-2007-0148695-A1, published Jun. 28, 2007; 5) PCT Application PCT/US04/042997, entitled "Optically encoded particles with grey scale spectra," to Sailor et al, filed Dec. 21, 2004, now U.S. Publication No. US-2007-0051815-A1, published Mar. 8, 2007; and 6) PCT Application PCT/US04/26572, entitled, "Photonic Sensor Particles and Fabrication Methods", to Sailor, et al filed Aug. 13, 2004, now U.S. Pat. No. 7,167,605, issued Jan. 23, 2007.

SUMMARY

The invention provides particles that produce a predetermined optical response and that may be manipulated magnetically. A preferred particle of the invention has a porous structure that produces a predetermined optical response and magnetic material adhered to the particle. Another preferred particle is amphiphilic. The optical response provided by a particle of the invention enables particles of the invention to be used in sensing, labeling, signaling, display and many other applications. An exemplary porous surface is a photonic crystal surface. The magnetic nature of the present magnetic particles permits the particles themselves to be manipulated, e.g., vibrated, moved and re-oriented. The particles can also be used to control, move, and/or deliver small volumes of liquids and solids associated with the particles.

DETAILED DESCRIPTION OF THE PREFERRED EMBODIMENTS

The invention provides magnetic porous particles. Particles of the invention have a porous surface and a magnetic surface. The surface has a predetermined optical response characteristic of a porosity in the material, e.g., silicon or another semiconductor. An exemplary porous surface is a photonic crystal surface. The optical response provided by a particle of the invention enables particles of the invention to be used in sensing, labeling, signaling, display and many other applications. The magnetic surface enhances the known uses for porous structures, and also provides for additional uses that will be recognized by artisans with reference to the detailed description herein. Generally, the magnetic nature of the present magnetic porous particles permits the particles themselves to be manipulated, e.g., vibrated, moved and re-oriented. The magnetic porous particles can also be used to control, move, and/or deliver small volumes of liquids and solids associated with the particles.

Magnetic porous particles of the invention can be fabricated from substrates of semiconductor or other suitable solid-state materials. Preferably, the substrate is a single-crystal material. A silicon (Si) crystal is a preferred substrate. Single crystal materials are preferred materials.

Embodiments of the invention provide magnetically switchable, micron-sized porous particles, and a method for fabrication of the same. More specifically, embodiments of the invention include porous particles having magnetic nanoparticles adhered thereto.

Particles of the invention are applicable to a variety of industries, including but not limited to drug discovery, biological screening, chemical screening, biological labeling, chemical labeling, in vivo labeling, security identification, signaling, displays, microfluidics and product marking. Various attributes of the particles and methods of the invention enable a wide range of applications in various industries. The small size of the particles facilitates ready incorporation into various hosts, e.g., products. test kits, assays, powders (such as explosives for identification), pastes, liquids, glass, paper, and any other host or system that can accept small particles. In vivo detection is enabled by biocompatible particles of the invention, such as silicon particles, which may then be queried, for example, through tissues using near infrared and infrared wavelengths that penetrate tissues.

Additionally, the particles of the invention have application to optical signaling and display applications. Particles of the invention provide a switchable optical display capability. The porous surface of a particle of the invention provides a strong predetermined optical response characteristic of the porosity of the material, and the magnetic surface does not. This is the basis for display or signaling. The optical response of an individual particle of the invention may be tailored to have a particular optical characteristic, e.g., to provide an optical response of a certain wavelength. Thus, for example, under control of a magnetic field, a particle or group of particles can be caused to produce an optical response of a particular color. Other particles, having a different photonic structure, may produce an optical response of a different color. The optical response of a particle may change in the presence of an analyte, permitting analyte detection.

Embodiments of the invention enable manipulation of liquids at the microscale without necessitating the addition of ions or other impurities to the bulk liquid in order to induce transport. Liquids may also be manipulated outside of traditional microfludic structures (as well as within such structures).

In a preferred embodiment magnetic porous particle of the invention, superparamagnetic nanoparticles, e.g., magnetite ($Fe_3O_4$), can be incorporated into the porous nanostructure. Preferred embodiment separate affinity particles have a first surface having a first affinity, e.g., a hydrophilic surface, and a second surface having a second affinity, e.g., a hydrophobic surface, allowing the materials to chaperone microliter-scale liquid droplets by application of an external magnetic field. The optical reflectivity spectrum response of the displays a peak that serves to identify the particle and the particle-liquid interaction. Other exemplary affinities can be created by, for example, incorporating a specific antibody, oligonucleotide or ligand to provide affinity for a specific antigen, oligonucleotide, or receptor.

In a preferred embodiment, photonic crystals particles are made from porous Si are with amphiphilic properties. Magnetic nanoparticles of $Fe_3O_4$ can be incorporated into the porous nanostructure. When placed in a two-phase liquid such as dichloromethane/water, these materials will accumulate and spontaneously align at the interface. If one of the liquids exists as small droplets in the other liquid, the particles can encapsulate the droplets, allowing the materials to chaperone microliter-scale liquid droplets by application of an external magnetic field. The optical reflectivity spectrum of the porous particle displays a peak that serves to identify the particle and the particle-liquid interaction.

In a preferred magnetic porous particle fabrication method of the invention, a multilayered porous dielectric mirror (rugate filter) is first etched into a single-crystal Si substrate. The film is then hydrosilylated to generate a chemically stable hydrophobic mirror. A second rugate filter with a different periodicity is etched into the substrate, immediately beneath the first rugate filter. The porous crystal film is released from the substrate. The porous crystal film is then divided into micron-sized particles by ultrasonication. Magnetic particles are infused into the second filter and impart a hydrophilic character to the second layer.

A particle formed by creating a particular porosity in a material, e.g., silicon, is a foundation for a method of fabrication of a magnetic porous particle of the invention. The particular porosity will govern the nature of the optical response of a magnetic porous particle of the invention. Particles may be encoded with different optical structures. Different optical structures can be etched prior to the adhering of the magnetic nanoparticles. Processes for creating different optical structures through creating porosity are described, for example, U.S. Published Patent Application 20050042764, entitled "Optically encoded particles" to Sailor et al., published Feb. 24, 2005; 2) U.S. Published Patent Application 20050009374, entitled "Direct patterning of silicon by photoelectrochemical etching", to Gao, et al., published Jan. 13, 2005, now U.S. Pat. No. 7,433,811, issued Oct. 7, 2008; 3) U.S. Published Patent Application 20030146109 entitled "Porous thin film time-varying reflectivity analysis of samples," to Sailor, et al. published Aug. 7, 2003, now U.S. Pat. No. 7,042,570 issued May 9, 2006; 4) PCT Application PCT/US04/043001, entitled "Optically encoded particles, system and high throughput screening, to Sailor et al, filed Dec. 21, 2004, now U.S. Publication No. US-2007-0148695-A1, published Jun. 28, 2007; 5) PCT Application PCT/US04/042997, entitled "Optically encoded particles with grey scale spectra," to Sailor et al, filed Dec. 21, 2004, now U.S. Publication No. US-2007-0051815-A1, published Mar. 8, 2007; and 6) PCT Application PCT/US04/26572, entitled, "Photonic Sensor Particles and Fabrication Methods", to Sailor, et al filed Aug. 13, 2004, now U.S. Pat. No. 7,167,605, issued Jan. 23, 2007.

The porosity of particles of the invention can have a complex structure that enables coding, for example. With varying porosity and multiple porosities in different layers, complex codes can be encoded in the porosity of a particle of the invention. Example codes realizable through control of the porosity of a particle are disclosed in U.S. Published Patent Application 20050042764, entitled "Optically encoded particles" to Sailor et al., published Feb. 24, 2005; and PCT Application PCT/US04/042997, entitled "Optically encoded particles with grey scale spectra," to Sailor et al. filed Dec. 21, 2004 now U.S. Publication No. US-2007-0051815-A1, published Mar. 8, 2007.

Figure 1:
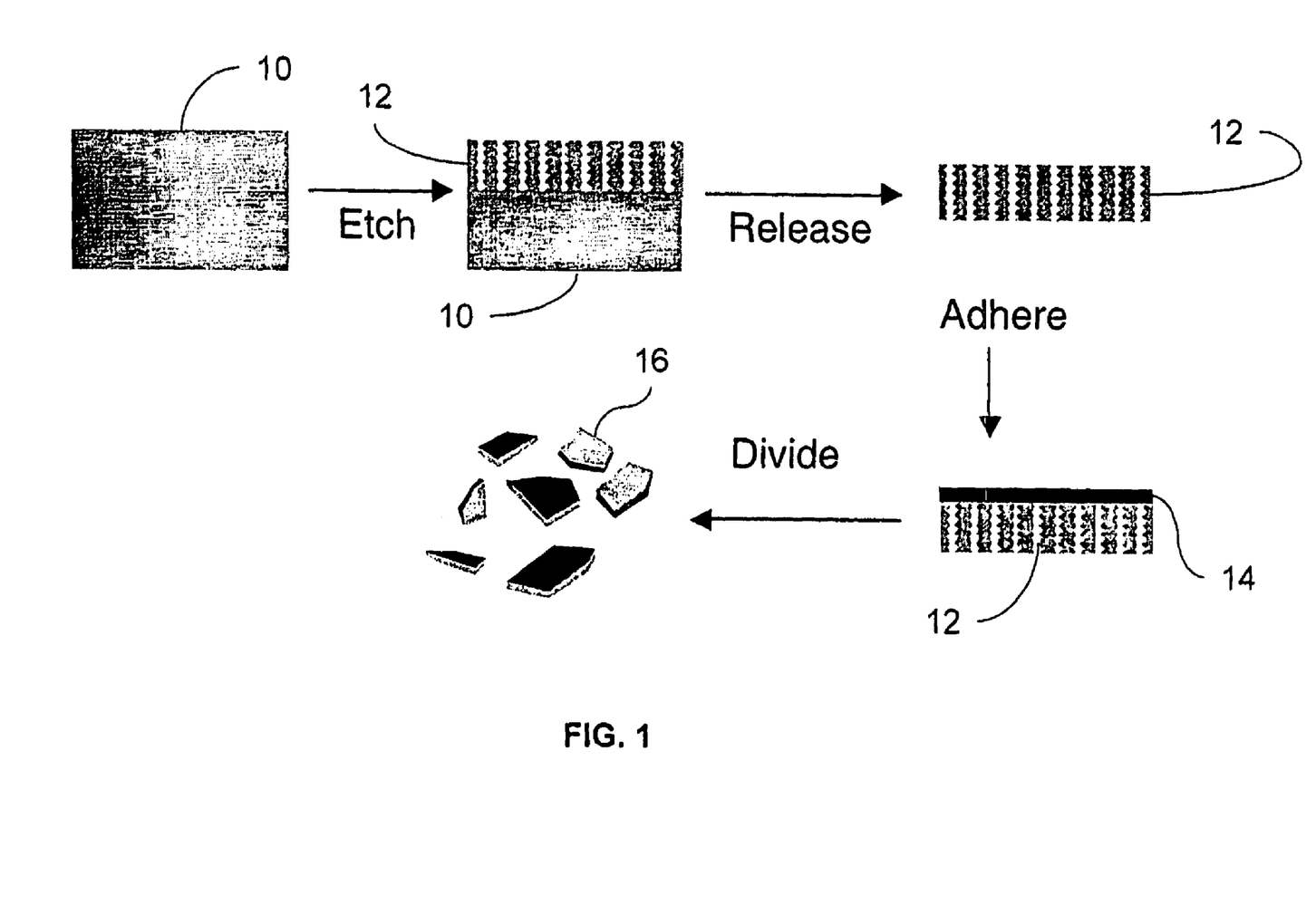
FIG. 1 illustrates a preferred method for forming magnetic porous particles according to the invention.

A preferred method of formation and a porous magnetic particle of the invention are illustrated in FIG. 1. A substrate 10, e.g., silicon or another semiconductor, is etched by a sinusoidal anodic etch. The etch is controlled to produce a crystal film 12 having a porosity having a characteristic optical response. The porous film 12 is released from the substrate 10. The release can be achieved, for example, by application of a current pulse. Magnetic nanoparticles 14, such as Fe nanoparticles commercially available from Nanomat, Inc. of North Huntingdon, Pa., are adhered to one side of the porous film 12. Upon drying, the magnetic nanoparticles 14 adhere sufficiently to the porous film 12. The film is then divided, for example by fracturing, into small magnetic porous particles 16. The particles 16 have, on one side, the porous film surface 12 and, on the other side, the magnetic material 14.

The magnetic porous particles 16 have microscopic dimensions. Preferred embodiment particles are formed from silicon, which is a biocompatible material, have a magnetic coating of Fe. This results in a magnetic coating on one side, which exhibits an insubstantial optical response, and a porous film on the other side, which exhibits a strong optical response, e.g., an intensely colored optical response. Other magnetic materials may also be used, e.g., rare earth magnetic materials, gadolinium, or nickel.

Figure 2:
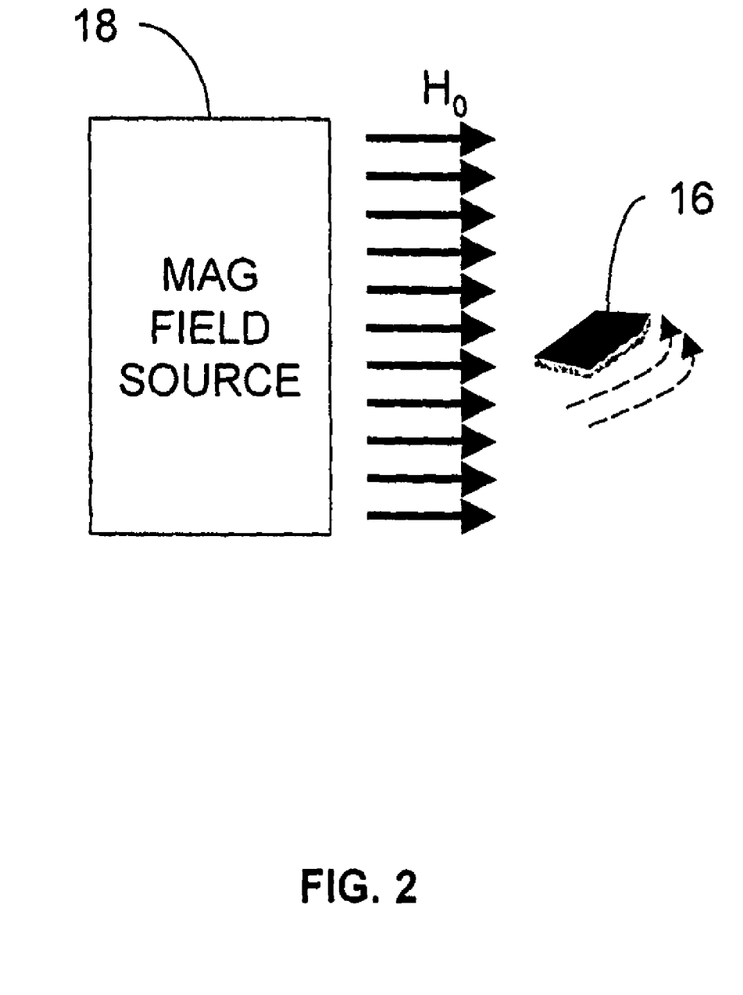
FIG. 2 illustrates a preferred method for manipulating magnetic porous particles according to the invention.

FIG. 2 illustrates an example method for manipulation of magnetic porous particles 16 of the invention. A magnetic porous particle 16 (or particles) of the invention is placed in an oscillating magnetic field created by a magnetic field source 18. The oscillating magnetic field $H_0$ causes the small particle 16 to vibrate, and at predetermined values of magnetic field strength and oscillation frequency, the porous particles can be induced to reorient, i.e., flip over to juxtapose the position of the magnetic side and the porous side of the particle 16.

The reflection of a laser beam impinging on particles of the invention can be used to quantify the rate of switching, with larger switching rates in smaller particles. Substantial switching rates are possible. In an exemplary experiment, switching of the particles at a rate of 175 Hz was demonstrated.

In addition to the vibration and reorientation of particles 16, magnetic field(s) may also be used to move particles 16 from one location to another, such as in a fluid medium, e.g., a microfluidic channel or a volume of liquid. Movement of particles by application of a magnetic field can be useful, for example, in optoelectronics, chemical and biological sensors, high-throughput screening, and drug delivery applications.

Magnetic porous particles may be used to bind and then release materials, including liquids and solids. Thus, other example applications of particles of the invention include microfluidics; transport of liquids and solids using magnetic fields; controlled manipulation of liquid or solid micro or nano particles; delivery, targeting, and controlled release of therapeutic and/or diagnostic reagents in a patient; high throughput screening of molecules for genomics, proteomics, drug discovery applications; and controlled manipulation of liquids containing cells, proteins, or other biological systems.

The formation method of FIG. 1 has been demonstrated with experiments. The invention is not limited to the experiments, but additional embodiments and inventive features will be apparent to artisans by reference to the experimental results that will now be described.

In the experiments consistent with the formation method of FIG. 1, multilayered porous silicon films were prepared by electrochemical etch of Si wafers (degenerate p-type, B doped, <1 mOhm-cm resistivity, polished on the (100) face, obtained from Siltronix, Inc.). The etching solution consisted of a 1:3 by volume mixture of absolute ethanol (Aldrich Chemicals) and aqueous 49% HF (Quantum Chemicals). Galvanostatic etching was carried out in a Teflon cell using a two-electrode configuration. The current density was modulated with a sine wave (typically between 12 and 35 mA/cm², 8.5 s periodicity, 70 repeats) to generate a periodically varying porosity gradient. The films were removed from the substrate by applying a 180 second pulse of current density 460 mA/cm² while the film was still immersed in the electrolyte solution. The film was then rinsed with ethanol and dried in air. Fe nanoparticles (8 nm average diameter, obtained from Nanomat Inc.), suspended in hexane were cast onto the porous Si multilayer film and the hexane was allowed to evaporate in air. The porous Si/Fe composite film was then fractured into small particles, yielding microscopic magnetic photonic crystals.

Magnetic porous particles produced by the above process were placed on a glass plate over a wire coil electromagnet wound around an iron core. The electromagnet was powered by a EG&G Princeton Applied Research 363 potentiostat operating in constant current mode, with an external source waveform supplied by the sinusoidal output from a Tektronix CFG 250 function generator. The waveform supplied ±400 mA to the magnet coil, producing a maximum field of approx. 600 mT. To measure the flipping rate of the magnetic particles in the oscillating magnetic field, the particles were illuminated with a 10 mW He/Ne laser and the reflected light intensity was measured as the photocurrent from an Ealing Electro-Optics Si photodiode. The photodiode signal was amplified with a Stanford Research Systems SR560 preamplifier, and recorded on a Tektronix TDS 520 digitizing oscilloscope.

Optical reflectivity spectra were obtained using a tungsten light source, optical microscope, and an Ocean Optics S2000 silicon CCD spectrometer fitted with a fiber optic input. The light collection end of the fiber optic was positioned at the focal plane of an optical microscope, allowing acquisition of spectra from a nominal spot size of 1 mm.

Photographs of ferromagnetic porous Si photonic crystal after formation revealed a green side that reflected the color characteristic of the photonic crystal, while the bottom side, coated with Fe nanoparticles, appeared black. The particles were flipped over in the experiments by application of an oscillating magnetic field.

Scanning electron microscope (SEM) images were obtained using an FEI Quanta 600 instrument operating at an accelerating voltage of 20 kV. An Oxford Instruments Energy Dispersive X-ray Spectrometer (EDS) was used to obtain qualitative elemental analysis of the Si and Fe nanoparticle layers. Cross-sectional scanning electron micrograph images (backscattered electron image) of a ferromagnetic porous Si photonic crystal produced by the above process before removal from the Si substrate showed a layer of Fe nanoparticles on top of a porous Si multilayer.

Figure 3:
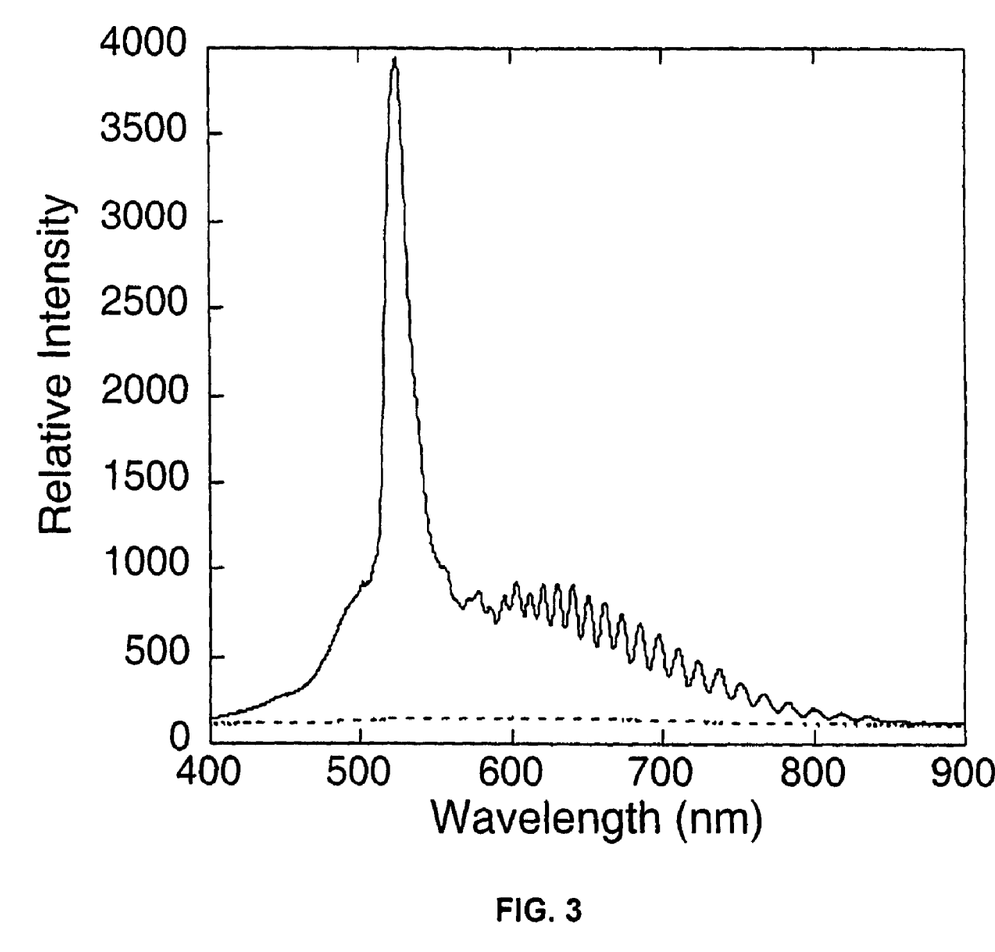
FIG. 3 shows white light reflection spectra taken from both sides of a magnetic porous silicon photonic crystal produced by experiments.

FIG. 3 shows white light reflection spectra taken from both sides of a magnetic porous Si photonic crystal produced by experiments. The intense and sharp reflectance peak expected for a rugate filter is observed on the photonic crystal side (solid trace, top), whereas a much weaker reflectance peak is detected on the side containing an over coating of Fe nanoparticles (dashed trace, bottom).

Figure 4:
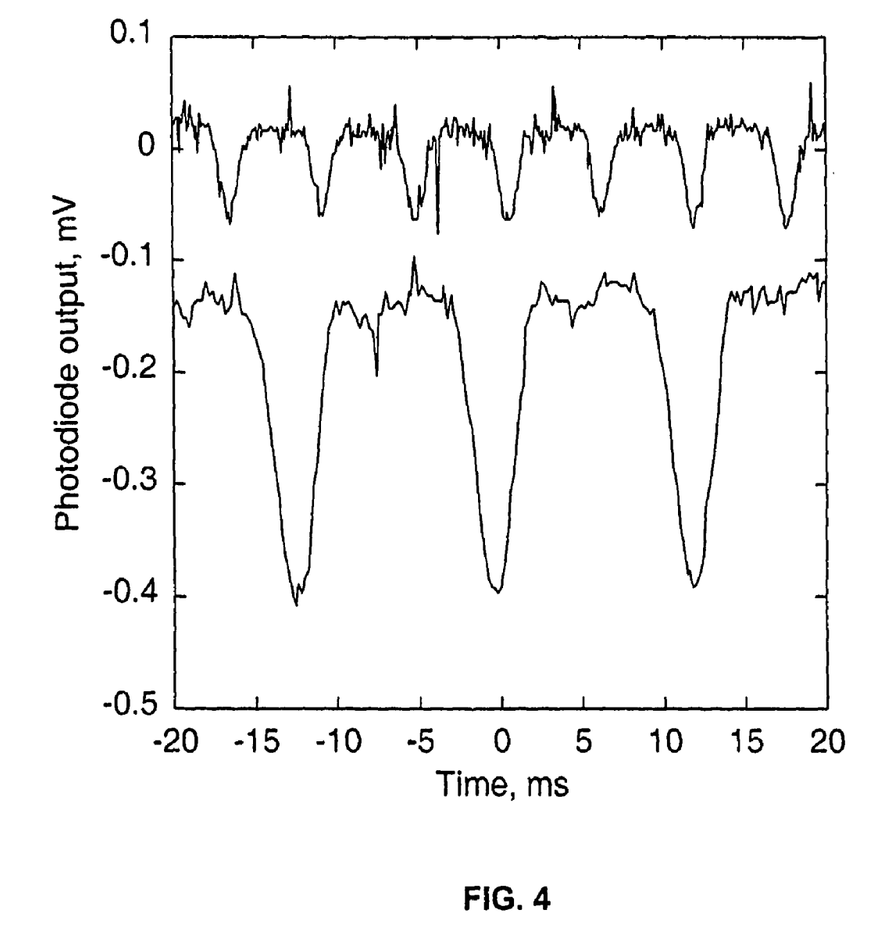
FIG. 4 is a plot of optical response versus time that illustrates a flipping rate of magnetic photonic crystal particles, measured by monitoring reflected laser light (632 nm, He/Ne) from a 100 micron (approx) particle.

FIG. 4 is a plot of optical response versus time that illustrates a flipping rate of a magnetic photonic crystal particles, measured by monitoring reflected laser light (632 nm, He/Ne) from a 100 micron (approx) particle. The magnetic photonic crystal ($\lambda_{max}$ of the photonic feature 632 nm) was subjected to an alternating magnetic field generated by an electromagnet. The reflected light was detected with an amplified photodiode connected to a digital oscilloscope. The bottom trace is recorded at a switching rate of 82 Hz. The top trace is the same particle recorded at a switching rate of 175 Hz. The bottom trace is offset by −0.2 V along the y-axis.

Another specific embodiment magnetic porous particle of the invention can self-assemble at a hydrophobic/hydrophilic interface. Such particles can effect controlled manipulation of small volumes of liquids, which has application in microfluidics for many high throughput analyses and micro assays.

Figure 5:
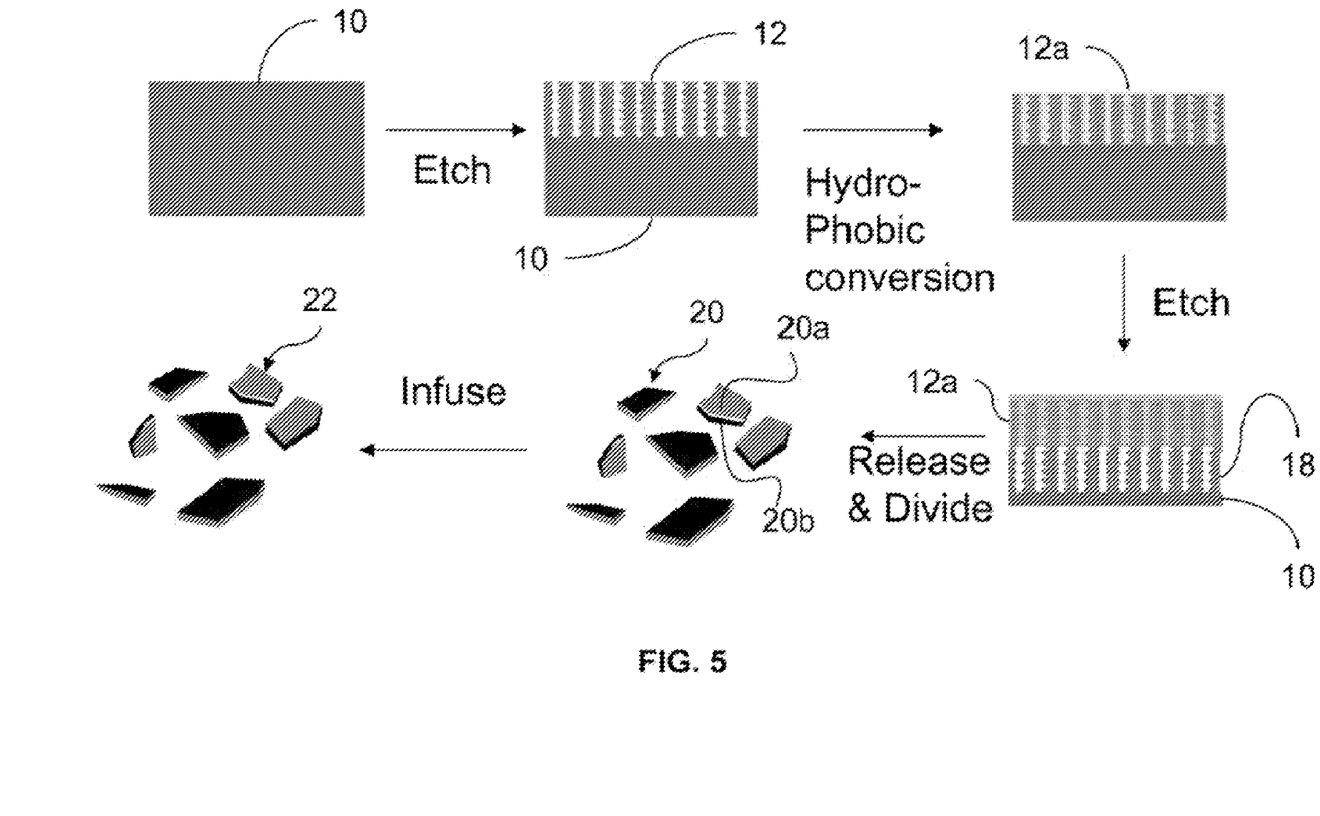
FIG. 5 illustrates a preferred method for forming magnetic porous particles having sides with separate affinities according to the invention.

FIG. 5 shows a preferred embodiment method of formation of magnetic porous particles with separate affinities. The process begins as the process does in FIG. 1, and like reference numerals will be used to indicated like elements in FIG. 5. A substrate 10, e.g., silicon or another semiconductor, is etched by a sinusoidal anodic etch. The etch is controlled to produce a crystal film 12 having a porosity having a characteristic optical response. In a preferred embodiment, the etch is carried out to achieve a sinusoidal variation in refractive index that results in a Rugate filter, which produces a sharp resonance feature in the optical reflectivity spectrum of the film, whose wavelength is determined by the periodicity and current limits used in the etch. The film 12 is then made to have a first affinity, e.g., by thermally hydrosilylating with 1-dodecene, generating a modified film 12a that is a chemically stable hydrophobic mirror. A second etch is carried out to form a second porous crystal film 18 having a different periodicity from the first film 12a. In a preferred embodiment, the etch is conducted such that the film 18 forms a second rugate filter, immediately beneath the first. Releasing and dividing the films 12a, 18 from the substrate 10 forms particles 20, having a porous crystal side that has a first affinity, e.g. is hydrophobic (in accordance with properties of the film 12a), and a side that has a second affinity, e.g. is hydrophilic (in accordance with the properties of the film 18). Magnetic nanoparticles are then infused into the one of the opposite flat sides 20a and 20b of the particle 20, e.g., side 20a of the particles to create magnetic porous particles 22 that have the separate affinities. Preferred embodiment separate affinity particles have a first surface having a first affinity, e.g., a hydrophilic surface, and a second surface having a second affinity, e.g., a hydrophobic surface, allowing the materials to chaperone microliter-scale liquid droplets by application of an external magnetic field. The optical reflectivity spectrum response of the displays a peak that serves to identify the particle and the particle-liquid interaction. Other exemplary affinities can be created by, for example, incorporating a specific antibody, oligonucleotide or ligand to provide affinity for a specific antigen, oligonucleotide, or receptor.

Experiments were conducted to demonstrate the method of FIG. 5. The invention is not limited to the experiments, but additional embodiments and inventive features will be apparent to artisans by reference to the experimental results that will now be described.

Multilayered porous Si dielectric mirrors were prepared by electrochemical etch of a single-crystal, (100)-oriented p-type Si wafer with a resistivity between 0.08 to 0.2 mOhm-cm, by application of a sinusoidal current waveform oscillating between 13.3 and 39.8 mA/cm$^2$. The periodicity of the waveform was 8 sec, repeated for 100 cycles in a 3:1 (v:v) aqueous 49% HF:ethanol solution. Thermal hydrosilylation was accomplished by placing the porous Si sample in liquid 1-dodecene (95%, Sigma-Aldrich Chemicals) in a Schlenk flask, degassing the liquid with 3 successive freeze-pump-thaw cycles, and then heating at 120° C. under nitrogen for two hours. A second rugate filter with a periodicity of 10 seconds was then etched into the substrate, immediately beneath the first layer for the same number of repeats. The porous Si structure was then removed from the crystalline Si substrate by application of a current pulse of ca. 15 mA/cm$^2$ in a 1:13.5 (v:v) aqueous 49% HF:ethanol solution for ca. 1 min, and the freestanding film was rinsed with ethanol and dried in an oven at 100° C.

Magnetite ($Fe_3O_4$) for infusion was prepared. In a representative preparation, 22 100 mL of a 1M aqueous $NH_4OH$ solution is added over a period of ten minutes to 10 mL of a 4:1 solution of 1M $FeCl_3$ and 2M $FeCl_2$ in water. The resulting black precipitate (magnetite) was filtered and then re-dispersed in 10 mL of 40 wt. % aqueous tetrabutylammonium hydroxide. Dynamic light scattering measurements indicated that the particles were ca. 30 nm in diameter.

The magnetite particles were then adhered to (trapped in) the film. The freestanding film was fractured by ultrasonication in ethanol and the resulting micro particles allowed to settle. The supernatant was removed, and the aqueous magnetite colloidal suspension was added. The high pH of the magnetite suspension spontaneously induces oxidation of the second porous Si layer, presumably trapping the magnetite nanoparticles in an oxide matrix. After isolation from the solution with the aid of an applied magnetic field, the microparticle composites are thermally oxidized to more completely trap the magnetite. Oxidation of the porous Si films was confirmed by Fourier transform infrared (FTIR) spectroscopy, and the presence and disposition of magnetite in the porous Si film is determined by FTIR and elemental mapping of iron in a cross-sectional electron microscope image using energy dispersive x-ray spectroscopy. Thermal oxidation preferentially produces oxide on the more reactive, hydrogen-terminated porous Si layer. The oxide imparts hydrophilic character to the second mirror while the hydrosilylated side retains its hydrophobic nature, allowing the particles to align at an aqueous/organic liquid interface.

To collect and oxidize particles, after stirring for 5 min, the magnetic porous Si photonic crystal particles were isolated from solution by removal with a bar magnet. While still being held in the flask with a magnet, the particles were rinsed several times with acetone to remove free magnetite nanoparticles. The isolated magnetic microparticles were then thermally oxidized in air at 100° C. for 1-2 h.

In a basic demonstration of a microfluidic application, the bifunctional magnetic microparticles were used to chaperone droplets of water immersed in an organic phase between a source and a drain. The microparticles spontaneously orient at the interface of a 30 microliter water droplet, with the hydrophilic side facing the aqueous phase. The interfacial adhesive forces are strong enough to allow the particles to move the droplet when a magnetic field is applied. When the droplet assembly is brought into contact with a glass capillary, water is removed from the assembly by capillary action. The magnetic porous Si chaperones can then be moved to a stainless steel syringe needle and refilled with liquid, completing the transport cycle.

The reflectivity spectrum from the bifunctional mirrors provides a signal that that can be used to identify the payload. The position of the spectral peaks in porous Si dielectric mirrors is a strong function of the average refractive index of the layers, and shifts in the wavelength of the spectral features have been shown to provide a very sensitive transduction modality for sensing condensable liquids, proteins, DNA, and other molecules. In example magnetic amphiphilic porous photonic crystal particles of the invention, the hydrosilylated layer displays a spectral wavelength maximum of 540 nm that shifts to 579 nm when it is immersed in hexane. The opposite side of the particle displays a band at 660 nm in air that shifts to 760 nm when immersed. The porous Si photonic crystals contain enough repeat layers (100) that cross-talk between opposite sides is not readily observed in the spectra.

Figure 6:
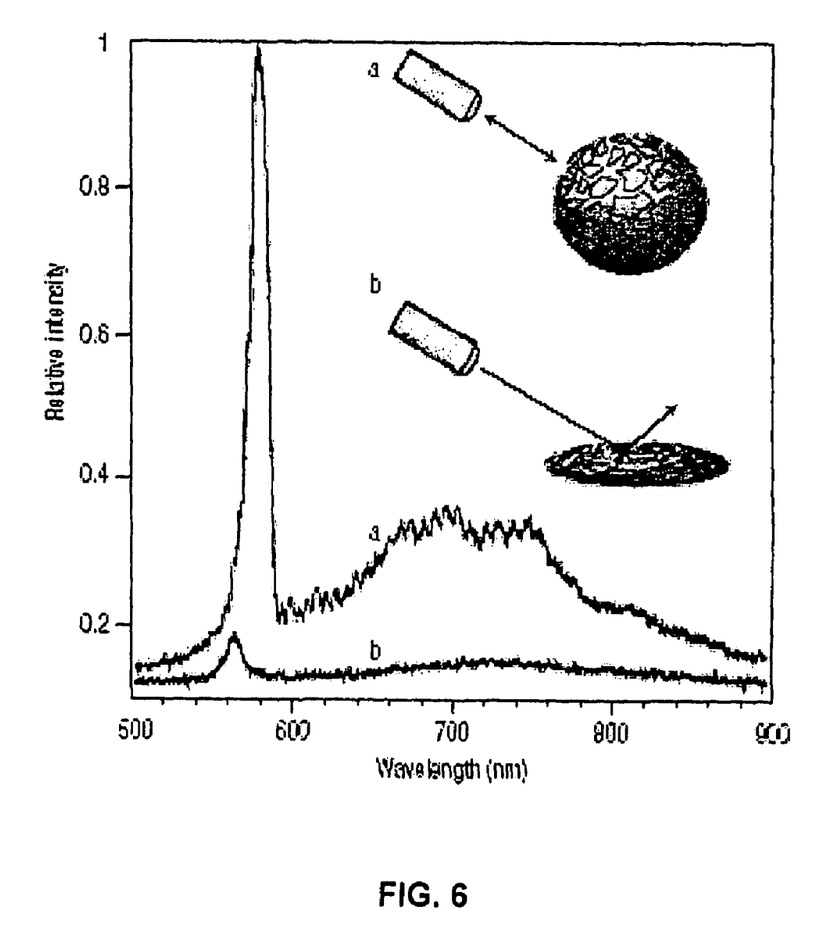
FIG. 6 shows reflectivity spectra of amphiphilic magnetic porous photonic crystal particles before and after delivery of payload, demonstrating fluidic transport by particles of the invention.

FIG. 6 shows reflectivity spectra of magnetic porous photonic amphiphilic particles before and after delivery of payload. In the A trace of FIG. 6, the reflectance spectrum was obtained from particles assembled on a water drop immersed in hexane. In the B trace of FIG. 6, the reflectance spectrum was obtained from the assembly after delivery of the aqueous payload to a capillary. Spectra were acquired using an Ocean Optics SD2000 CCD (charge-coupled device) spectrometer fitted with focusing optics and using a tungsten light source coaxial with the detection optics. The detection optics were positioned as indicated in the inset.

The approximate spherical shape of the water droplet/chaperone assembly leads to a strong reflection from the hydrophobic side over a large range of incident angles FIG. 6, trace a. Upon delivery of the aqueous payload, the sphere is deflated and reflection from the assembly is dramatically reduced in intensity, FIG. 6, trace b. These spectral characteristics can thus indicate the identity of the chaperones and the status of the chaperoned droplet.

Figure 7A:
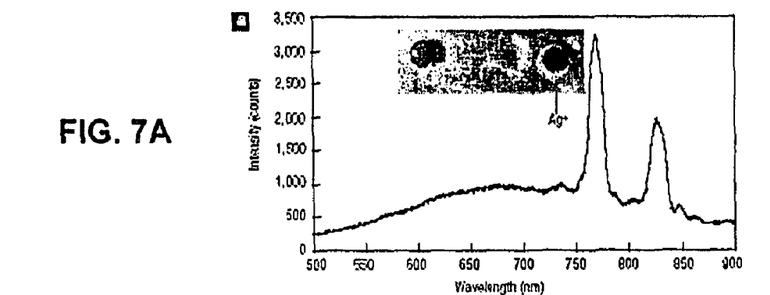
FIGS. 7A-7C show reflectivity spectra of two sets of amphiphilic magnetic porous photonic crystal particle chaperones involved in mixing chemicals to perform a reaction.
Figure 7B:
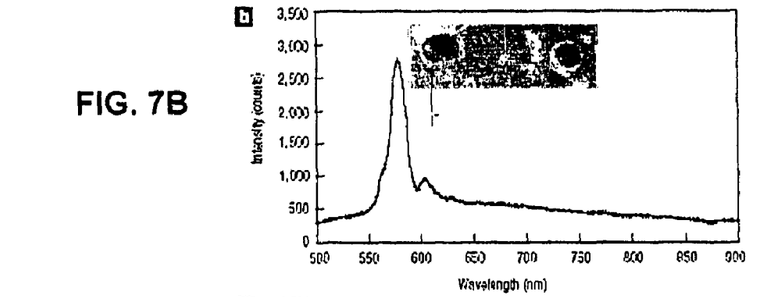
Figure 7C:
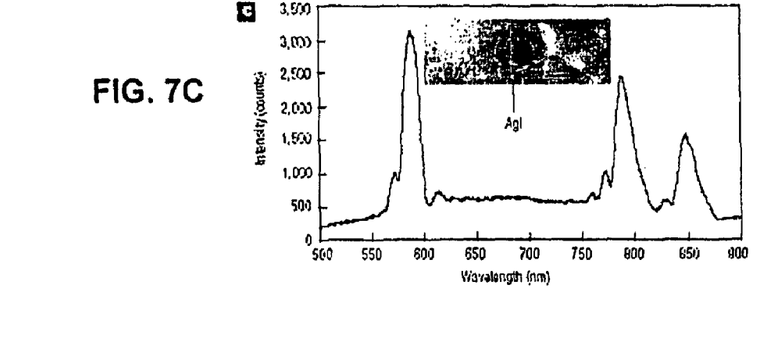

FIGS. 7A-7C show reflectivity spectra of two sets of magnetic amphiphilic porous Si chaperones involved in mixing chemicals to perform a reaction. The inset of each spectrum shows a photograph of the experiment representing that stage of the reaction. The FIG. 7A reflectance spectrum was obtained from particles assembled on a water droplet (4 mm diameter) containing Ag+ (aq). The particles on this droplet contained a spectral code consisting of two peaks. In FIG. 7B, the reflectance spectrum was obtained from a water droplet containing I(aq) and the particles had a separate spectral code consisting of a single peak. In FIG. 7C, the reflectance was spectrum obtained from water droplet after the two drops were combined under the force of a magnet, showing the superposition of the two spectral codes. The AgI(s) product of the reaction is apparent in the image as a white cloud inside the drop. Water droplets were immersed in octadecene throughout the experiments.

The method presented here provides a general technique for manipulating small volumes of liquids without a microfluidic container. Because the magnetic porous Si particles adhere to the surface of the water drop, they do not require a specific payload composition such as a high ionic strength in order to effect liquid motion. The electrochemical synthesis of porous Si photonic crystals allows the incorporation of spectral bar codes (see, e.g., U.S. Published Patent Application 20050042764, entitled "Optically encoded particles" to Sailor et al., published Feb. 24, 2005), allowing the possibility of distinguishing between multiple distinct liquid drops in combinatorial assays. Since either water or an organic liquid can be encapsulated by the amphiphilic particles, a wide range of inorganic or organic molecules can be manipulated for the purpose of carrying out micro reactions. Mammalian or bacterial cells can also be incorporated in this system for cell-based assays. In addition, a wide range of molecules can be incorporated within the porous nanostructure of the magnetic porous Si particles, allowing controlled manipulation of very small amounts of chemical reagents.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A method of fabricating magnetic porous particles, the method comprising steps of:
   providing a substrate;
   etching the substrate to create a film having a porous photonic structure;
   releasing the film from the substrate;
   dividing the film into particles; and
   magnetizing only one side of the film prior to said step of dividing or only one side of the particles after said step of dividing.

2. The method of claim 1, wherein said step of magnetizing comprises adhering magnetic nanoparticles to the only one side of the film prior to said step of dividing.

3. The method of claim 2, wherein said step of adhering comprises depositing magnetic nanoparticles on or within the pores of the only one side of the film.

4. The method of claim 1, further comprising applying a magnetic field to the particles to manipulate the particles.

5. The method of claim 1, wherein the substrate comprises a silicon substrate.

6. The method of claim 3, wherein the magnetic nanoparticles comprise Fe nanoparticles.

7. The method of claim 1, wherein said step of magnetizing comprises infusing magnetic material into the pores of the only one side of the particles after said step of dividing.

8. The method of claim 7, further comprising steps of:
   after said step of etching, treating the film to create a first affinity on a side opposite said only one side of said film;
   prior to said step of releasing, further etching the substrate to create a different porous photonic structure and a second affinity on said only one side of said film.

9. The method of claim 8, wherein said step of infusing comprises infusing magnetite into the only one side of the particles after said step of dividing.

10. A magnetic porous film particle, the particle comprising:
    a porous film with opposite flat surfaces, a first one of said opposite flat surfaces having a porosity that produces a predetermined optical response; and
    a second one of said opposite flat surfaces being a magnetic surface that has an insubstantial or no optical response.

11. The particle of claim 10, wherein one of said magnetic surface and said porous surface is hydrophobic and the other is hydrophilic.

12. The particle of claim 10, wherein said magnetic surface comprises a second porous surface having a second porosity, said second surface having adhered or infused magnetic material.

13. A magnetic porous particle, the particle comprising:
    porous material having a porosity that produces a predetermined optical response; and
    magnetic material adhered to or infused in only one side of the porous material, wherein said magnetic surface comprises a second porous surface having a second porosity, said second surface having adhered or infused magnetic material and the magnetic material comprises magnetic nanoparticles.

14. The particle of claim 13, wherein the magnetic nanoparticles comprise $Fe_3O_4$ nanoparticles.

15. A magnetic porous particle, the particle comprising:
    porous material having a porosity that produces a predetermined optical response; and
    magnetic material adhered to or infused in only one side of the porous material, wherein the magnetic material comprises magnetic nanoparticles.

16. The particle of claim 15, wherein the magnetic nanoparticles comprise $Fe_3O_4$ nanoparticles.

17. A method of producing a display, the method comprising magnetically manipulating a particle of claim 15 to selectively produce one of the predetermined optical response and the insubstantial or no optical response.

18. The method of claim 17, further comprising a step of switching, by magnetically manipulating, between the predetermined optical response and the insubstantial or no optical response.

19. A method of fabricating magnetic porous particles, the method comprising steps of:
electrochemically etching a first side of semiconductor wafer by application of a sinusoidal current waveform to the wafer when it is in an etching solution to create a first porous surface;
hydrosilylating the first porous surface to make the first porous surface hydrophobic and chemically stable;
electrochemically etching the semiconductor wafer immediately beneath the first porous surface to create a second porous surface that is hydrophilic;
releasing a porous film having the first and second porous surfaces from the semiconductor wafer;
magnetizing the second porous surface by placing the porous film in a magnetite nanoparticle suspension to induce oxidation of the second porous surface and adherence of magnetite nanoparticles to the second porous surface.

20. The method of claim 19, further comprising a step of fracturing the porous film into particles.

21. The method of claim 20, wherein said step of fracturing comprises ultrasonication.

22. The method of claim 21, further comprising a step of thermally oxidizing the second porous surface to more completely trap the magnetite nanoparticles.

* * * * *

UNITED STATES PATENT AND TRADEMARK OFFICE
CERTIFICATE OF CORRECTION

PATENT NO. : 8,097,173 B2  
APPLICATION NO. : 11/632914  
DATED : January 17, 2012  
INVENTOR(S) : Sailor et al.

Page 1 of 1

It is certified that error appears in the above-identified patent and that said Letters Patent is hereby corrected as shown below:

In the Specification:

Col. 4, line 61    After "2004" and before "now", please insert a --,--.

Signed and Sealed this  
Twenty-ninth Day of May, 2012

David J. Kappos  
*Director of the United States Patent and Trademark Office*